US012779407B2

(12) United States Patent
Bhatnagar et al.

(10) Patent No.: US 12,779,407 B2
(45) Date of Patent: Nov. 3, 2026

(54) PROCESS FOR PREPARING A POLY(ARYL ETHER SULFONE) (PAES) POLYMER

(71) Applicant: SYENSQO SPECIALTY POLYMERS USA, LLC, Alpharetta, GA (US)

(72) Inventors: Atul Bhatnagar, Alpharetta, GA (US); David B. Thomas, Milton, GA (US)

(73) Assignee: SYENSQO SPECIALTY POLYMERS USA, LLC, Alpharetta, GA (US)

( * ) Notice: Subject to any disclaimer, the term of this patent is extended or adjusted under 35 U.S.C. 154(b) by 762 days.

(21) Appl. No.: 17/781,099

(22) PCT Filed: Dec. 4, 2020

(86) PCT No.: PCT/EP2020/084709
§ 371 (c)(1),
(2) Date: May 31, 2022

(87) PCT Pub. No.: WO2021/110954
PCT Pub. Date: Jun. 10, 2021

(65) Prior Publication Data

US 2023/0001362 A1 Jan. 5, 2023

Related U.S. Application Data

(60) Provisional application No. 62/944,121, filed on Dec. 5, 2019.

(30) Foreign Application Priority Data

Mar. 10, 2020 (EP) .................................... 20162138

(51) Int. Cl.
*B01D 71/68* (2006.01)
*A61M 1/34* (2006.01)
*B01D 61/24* (2006.01)
*B01D 69/08* (2006.01)

(52) U.S. Cl.
CPC ........... *B01D 71/68* (2013.01); *B01D 61/243* (2013.01); *B01D 69/08* (2013.01); *A61M 1/3413* (2013.01)

(58) Field of Classification Search
None
See application file for complete search history.

(56) References Cited

U.S. PATENT DOCUMENTS

| | | | | |
|---|---|---|---|---|
| 9,199,205 | B2 | 12/2015 | Weber et al. | |
| 2014/0113093 | A1 | 4/2014 | Corbin et al. | |
| 2015/0122121 | A1 * | 5/2015 | McGrath | B01D 71/80 96/10 |
| 2018/0346710 | A1 | 12/2018 | Yasunaga et al. | |
| 2019/0106545 | A1 | 4/2019 | Russell et al. | |

FOREIGN PATENT DOCUMENTS

| | | | | |
|---|---|---|---|---|
| CN | 105745277 | A | 7/2016 | |
| EP | 1678166 | B1 | 7/2009 | |
| GB | 2025312 | A * | 1/1980 | B01D 63/0233 |
| JP | S58101113 | A | 6/1983 | |
| JP | S58101114 | A | 6/1983 | |
| JP | S6210134 | A | 1/1987 | |
| JP | S63268737 | A | 11/1988 | |
| JP | 2008222777 | A | 9/2008 | |
| JP | 2014517863 | A | 7/2014 | |
| JP | 2017523918 | A | 8/2017 | |
| JP | 2019501013 | A | 1/2019 | |
| WO | 08103599 | A2 | 8/2008 | |
| WO | WO2012/158795 | A1 | 11/2012 | |
| WO | WO 2012160172 | A1 | 11/2012 | |
| WO | WO 2015/066496 | A1 | 5/2015 | |
| WO | WO 2015173257 | A1 | 11/2015 | |
| WO | WO 2017096140 | A1 | 6/2017 | |
| WO | 2018079733 | A1 | 5/2018 | |
| WO | 2019048652 | A1 | 3/2019 | |

OTHER PUBLICATIONS

Sundell et al. (Polymer 55, 2014, p. 5623-5634). "Synthesis, oxidation and crosslinking of tetramethyl bisphenol F (TMBPF)-based polymers for oxygen/nitrogen gas separations". (Year: 2014).*

Sundell et al. "Synthesis, oxidation and crosslinking of tetramethyl bisphenol F (TMBPF)-based polymers for oxygen/nitrogen gas separations" Polymer, 55, 2014, p. 5623-5634 (Year: 2014).*

Sundell B. J. et al., "Synthesis, oxidation and crosslinking of tetramethyl bisphenolF (TMBPF)-based polymers for oxygen/nitrogen gas separations", Polymer, 2014, vol. 55, pp. 5623-5634, Elsevier Ltd.

Sun H. et al., "Self-crosslinked alkaline electrolyte membranes based on quaternary ammonium poly (ether sulfone) for high-performance alkaline fuel cells", International Journal of Hydrogen Energy, 2012, vol. 37 (12), pp. 9873-9881, Elsevier Ltd.

McHattie, J. S., "Chapter 9 Isopropylidene replacment for tetramethyl polysulfone, PhD Dissertation", 1990, pp. 165-197, University of Texas, Austin, TX, US.

McHattie, J. S. et al., "Gas transport properties of polysulfones: 3. Comparison of tetramethyl-substituted bisphenols", Polymer, 1992, vol. 33 (8), pp. 1701-1711, Butterworth-Heinemann Ltd.

Aitken, C. L. et al., "Dynamic mechanical behavior of polysulfones", Macromolecules, 1992, vol. 25 (11), pp. 2910-2922, American Chemical Society.

(Continued)

*Primary Examiner* — Ryan B Huang

(74) *Attorney, Agent, or Firm* — Beatrice C. Ortego

(57) ABSTRACT

The present invention relates to a membrane for purifying a biological fluid, comprising at least one poly(aryl ether sulfone) (PAES) polymer based on one specific dihydroxy monomer. The present invention also relates to a purification method for a biological fluid comprising at least a filtration step through this membrane, as well as to the polymer solution for preparing such membrane, comprising this PAES.

18 Claims, 1 Drawing Sheet

(56) References Cited

OTHER PUBLICATIONS

Zhensheng, M. et al., "Anion-Conductive Membranes with Ultralow Vanadium Permeability and Excellent Performance in Vanadium Flow Batteries", ChemSusChem, 2013, vol. 6(2), pp. 328-335, Wiley-VCH Verlag GmbH&Co. KGaA, Weinheim.

Sundell, B. J., "Chapter 6: Synthesis, oxidation and crosslinking of tetramethyl bisphenol F (TMBPF)-based polymers for oxygen/nitrogen gas separations", PhD Dissertation, 2014, pp. 206-240, Virginia Polytechnic Institute and State University, Blacksburg, VA, US.

Camacho-Zuniga, C., "Aromatic polysulfone copolymers for gas separation membrane applications", Journal of Membrane Science, 2009, pp. 221-226, Elsevier B.V.

Organic Chemistry, $7^{th}$ Edition, 2014, by P. Y. Bruice, Pearson, Chapter 15: NMR Spectroscopy, p. 660.

"Alkylene." Merriam-Webster.com Dictionary, Merriam-Webster, https://www.merriam-webster.com/dictionary/alkylene, accessed online on Jul. 28, 2025.

Richard W. Baker (2004). *Membrane Technology and Applications*. John Wiley & Sons Ltd. p. 4, 5, 303, 304.

* cited by examiner

PROCESS FOR PREPARING A POLY(ARYL ETHER SULFONE) (PAES) POLYMER

RELATED APPLICATIONS

This application is a U.S. national stage entry under 35 U.S.C. § 371 of International Application No. PCT/EP2020/084709 filed Dec. 4, 2020, which claims priorities of U.S. provisional application No. 62/944,121 filed on Dec. 5, 2019, and of EP patent application No. 20162138.0 filed on Mar. 10, 2020, the whole content of each of these applications being incorporated herein by reference for all purposes.

TECHNICAL FIELD

The present invention relates to a membrane for purifying a biological fluid, comprising at least one poly(aryl ether sulfone) (PAES) polymer based on one specific dihydroxy monomer. The present invention also relates to a purification method for a biological fluid comprising at least a filtration step through this membrane, as well as to the polymer solution for preparing such membrane, comprising this PAES.

BACKGROUND ART

Poly(aryl ether sulfone) (PAES) polymers have been utilized for making products in different fields of applications, for instance in the medical market, such as membranes due to their excellent mechanical and thermal properties, coupled with outstanding hydrolytic stability. PAES is a generic term used to describe any polymer containing at least one sulfone group (—SO2-), at least one ether group (—O—) and at least one arylene group.

A commercially important group of PAES includes polysulfone polymers identified herein as polysulfones, in short PSU. PSU polymers contain recurring units derived from the condensation of the dihydroxy monomer bisphenol A (BPA) and a dihalogen monomer, for example 4,4'-dichlorodiphenyl sulfone (DCDPS). Such PSU polymers are commercially available from Solvay Specialty Polymers USA LLC under the trademark UDEL®. The structure of the repeating units of such a PSU polymer is shown below:

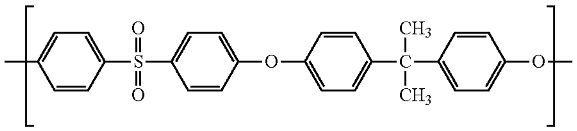

PSU polymers have a high glass transition temperature (e.g., about 185° C.) and exhibit high strength and toughness.

Another important group of PAES includes polyethersulfone polymers, in short PES. PES polymers derive from the condensation of the dihydroxy monomer bisphenol S (BPS) and a dihalogen monomer, for example 4,4'-dichlorodiphenyl sulfone (DCDPS). Such PES polymers are commercially available from Solvay Specialty Polymers USA LLC under the trademark VERADEL®. The structure of the repeating units of such a PES polymer is shown below:

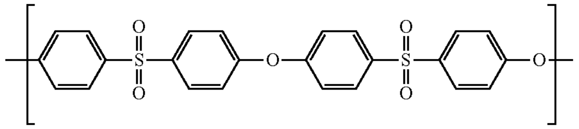

BPA and BPS are industrial chemicals that have been present in many articles, including plastic bottles and food and beverage cans since the 1960s. PSU and PES polymers, respectively based on BPA and BPS, are also frequently used to prepare membranes to be used in contact with biological fluids, for example blood. In recent years, concerns have been raised about BPA and BPS's safety. There is therefore a need for polymeric materials based on monomers distinct from BPS and BPA.

The membrane described in the present invention is based on a PAES polymer which is BPA and BPS free. More precisely, the PAES of the present invention is preferably based on tetra-alkylated bisphenol F, for example tetramethyl bisphenol F (TMBPF), which has low or no endocrine disruption potential.

US 2014/0113093 (Solvay) describes PAES polymers derived from specific aromatic diols, which have weak binding affinity for estrogen receptors and are well-suited for the food and drugs industry, advantageously having a lower risk for human health. This document does not describe the use of tetra-alkylated bisphenol F.

The article of Sundell et al. (Polymer (2014), 55(22), 5623-5634) describes the synthesis, oxidation and crosslinking of tetramethyl bisphenol F (TMBPF)-based polymers for oxygen/nitrogen gas separations.

The article of Sun et al. (International Journal of Hydrogen Energy (2012), 37(12), 9873-9881) relates to self-crosslinked alkaline electrolyte membranes based on quaternary ammonium poly(ether sulfone) for high-performance alkaline fuel cells, and notably describes the synthesis of tetramethylbisphenol F polysulfone from TMBPF and DCDPS in the presence of potassium carbonate, dimethylsulfoxide and toluene.

These articles however do not describe the use of such polymers to prepare membranes for purifying biological fluids. Notably these documents do not describe a method for purifying a biological fluid comprising at least a filtration step through such membranes.

WO 2018/079733 (Mitsui) relates to a forward osmosis membrane comprising a semipermeable membrane and a porous substrate disposed on at least one side thereof. The semipermeable membrane comprises a protonic acid group-containing aromatic polyether resin. The copolymer of example 8 results from the condensation of 40 mol. % disulfonated DCDPS and 60 mol. % of DCDPS with TMBPF in a DMSO/toluene solvent blend. Such copolymer however presents a too low molecular weight which makes it unsuitable for the preparation of membranes.

WO17096140 (GE) relates generally to polymer blends used for making hollow fiber membranes. The polymer blends comprise at least one polymer comprising zwitterionic groups. US 2019/106545 (Fresenius), relates to a polysulfone-urethane copolymer, as well as methods are disclosed for incorporating the copolymer in membranes (e g., spun hollow or flat membranes). US 2014/113093 (Solvay) relates to new polymers having reduced estrogenic activity. The invention further relates to compositions containing such polymers, and articles made from such polymers. None of these three documents describe a polymer according to the present invention.

SUMMARY OF INVENTION

An aspect of the present disclosure is directed to a membrane for purifying a biological fluid, comprising a poly(aryl ether sulfone) (PAES) polymer comprising recurring units ($R_{PAES}$) of formula (I):

(I)

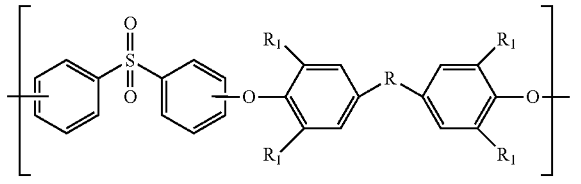

wherein:

each $R_1$ is, independently at each location, an alkyl having from 1 to 5 carbon atoms, and R is an alkylene having from 1 to 10 carbon atoms or a cycloalkylene having from 5 to 8 carbon atoms.

The PAES used to prepare such membrane is preferably derived from the condensation in a reaction mixture ($R_G$) of:

at least one aromatic dihydroxy monomer (a), comprising at least the monomer (a1) of formula (III):

(III)

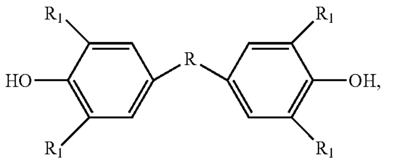

wherein each $R_1$ is, independently at each location, an alkyl having from 1 to 5 carbon atoms, and R is an alkylene having from 1 to 10 carbon atoms or a cycloalkylene having from 5 to 8 carbon atoms, at least one aromatic dihalogen sulfone monomer (b), comprising at least one dihalogen compound selected from the group consisting of 4,4'-dichlorodiphenyl sulfone (DCPDS) and 4,4'-difluorodiphenyl sulfone (DFDPS), at least one carbonate component, in a solvent.

Another aspect of the present invention is a purification method for a biological fluid comprising at least a filtration step through the membrane described herein. The biological fluid is preferably blood. The method is preferably carried out by means of an extracorporeal circuit, for example a hemodialyzer.

A further aspect of the present invention is a polymer solution for preparing a membrane, comprising the herein disclosed PAES.

A fourth aspect of the present invention is the use of the PAES polymer described herein to prepare a membrane for purifying a biological fluid, preferably blood.

DISCLOSURE OF INVENTION

Figure 1:
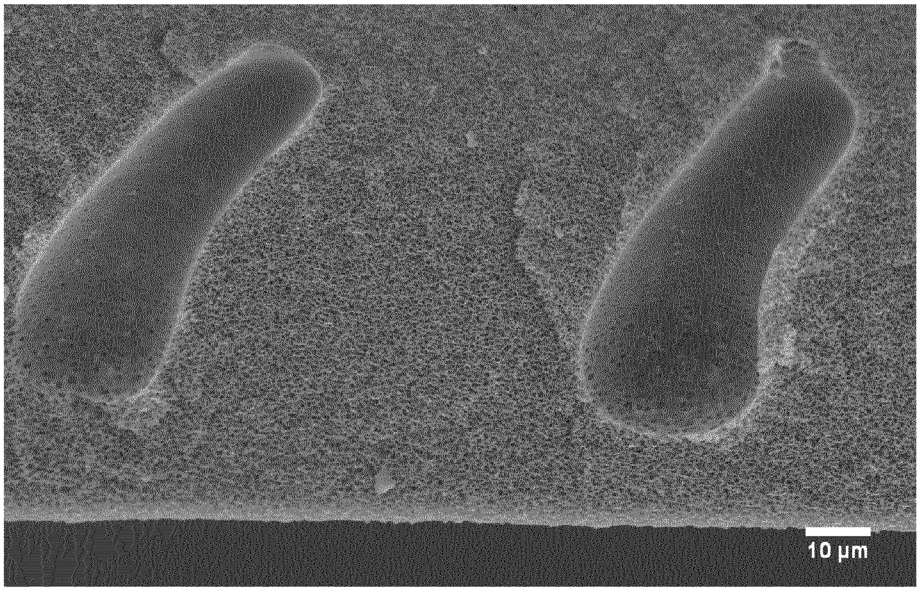
FIG. 1 is a picture of the membrane obtained with a polymer according to the invention (scale 50 μm)

The inventors have found that certain dihydroxy monomers which have low or no endocrine disruption potential can be used to successfully prepare PAES polymers with the right set of properties (notably molecular weight), which can then be used to prepare membranes to be used for purifying biological fluids. Therefore they have lower risks for human health, as the PAES polymers incorporating such monomers exhibit reduced estrogenic activities.

In the present application:

any description, even though described in relation to a specific embodiment, is applicable to and interchangeable with other embodiments of the present disclosure;

where an element or component is said to be included in and/or selected from a list of recited elements or components, it should be understood that in related embodiments explicitly contemplated here, the element or component can also be any one of the individual recited elements or components, or can also be selected from a group consisting of any two or more of the explicitly listed elements or components; any element or component recited in a list of elements or components may be omitted from such list; and any recitation herein of numerical ranges by endpoints includes all numbers subsumed within the recited ranges as well as the endpoints of the range and equivalents.

The expressions "(co)polymer" or "polymer" are hereby used to designate homopolymers containing substantially 100 mol. % of the same recurring units and copolymers comprising at least 50 mol. % of the same recurring units, for example at least about 60 mol. %, at least about 65 mol. %, at least about 70 mol. %, at least about 75 mol. %, at least about 80 mol. %, at least about 85 mol. %, at least about 90 mol. %, at least about 95 mol. % or at least about 98 mol. %.

The Polymer PAES

The poly(aryl ether sulfone) (PAES) polymer described in the present disclosure comprises recurring units ($R_{PAES}$) of formula (I):

(I)

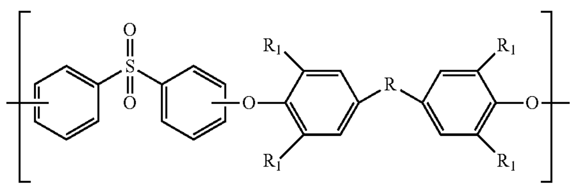

wherein:

each $R_1$ is, independently at each location, an alkyl having from 1 to 5 carbon atoms, and R is an alkylene having from 1 to 10 carbon atoms or a cycloalkylene having from 5 to 8 carbon atoms.

In some embodiments, the PAES polymer comprises at least 50 mol. % of recurring units ($R_{PAES}$), based on the total number of moles in the PAES polymer.

The PAES polymer of the present invention can therefore be a homopolymer or a copolymer. If it is a copolymer, it can be a random, alternate or block copolymer.

According to an embodiment of the present invention, at least 50 mol. %, at least 60 mol. %, at least 70 mol. %, at least 80 mol. %, at least 90 mol. %, at least 95 mol. %, at least 99 mol. % or all of the recurring units in the PAES are recurring units ($R_{PAES}$) of formula (I). Preferably, the PAES polymer of the present invention comprises more than 60 mol. % of recurring units ($R_{PAES}$), based on the total number of moles in the PAES polymer.

The PAES polymer of the present invention preferably comprises recurring units ($R_{PAES}$) of formula (II):

(II)

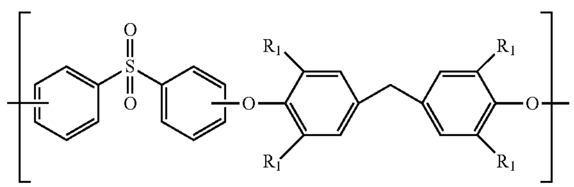

wherein each $R_1$, independently at each location, is an alkyl having from 1 to 5 carbon atoms, preferably methyl at each location.

According to a preferred embodiment of the present invention, at least 50 mol. %, at least 60 mol. %, at least 70 mol. %, at least 80 mol. %, at least 90 mol. %, at least 95 mol. %, at least 99 mol. % or all of the recurring units in the PAES are recurring units ($R_{PAES}$) of formula (II).

In some embodiments of the present invention, the PAES comprises recurring units ($R^*_{PAES}$) which are distinct from the ($R_{PAES}$) recurring units of formula (I) or (II).

When the PAES comprises recurring units ($R^*_{PAES}$) which are distinct from the ($R_{PAES}$) recurring units of formula (I) or (II), this additional recurring units may for example be sulfonated. If the polymer comprises sulfonated recurring units ($R^*_{PAES}$) obtained from the condensation of disulfonated DCDPS, the number of moles of these recurring units is less than 40 mol. %, for example less than 30 mol. %, less than 25 mol. %, less than 20 mol. %, less than 15 mol. % or less than 10 mol. %, based on the total number of moles in the PAES polymer.

In some other embodiments, the PAES may comprise recurring units ($R^*_{PAES}$) which are distinct from the ($R_{PAES}$) recurring units of formula (I) or (II), with the proviso that when it does, the mole ratio of sulfonated recurring units is less than 1 mol. %, less than 0.5 mol. %, or less than 0.1 mol. %, based on the total number of moles in the PAES polymer.

In some embodiments, the PAES polymer of the present disclosure comprises recurring units ($R_{PAES}$) of formula (I) or (II) and less than 40 mol. %, less than 30 mol. %, less than 25 mol. %, less than 20 mol. %, less than 15 mol. %, less than 10 mol. %, less than 1 mol. % of sulfonated recurring units, less than 0.5 mol. % or even less than 0.1 mol. %, based on the total number of moles in the PAES polymer.

The PAES polymer described in the present disclosure can be obtained by the condensation in a reaction mixture ($R_G$) of:

at least one aromatic dihydroxy monomer (a), comprising at least the monomer (a1) of formula (III):

(III)

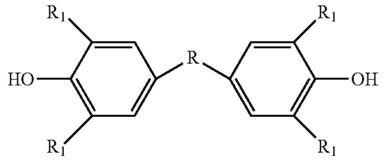

wherein each $R_1$, independently at each location, is an alkyl having from 1 to 5 carbon atoms, and R is an alkylene having from 1 to 10 carbon atoms or a cycloalkylene having from 5 to 8 carbon atoms, at least one aromatic dihalogen sulfone monomer (b), comprising at least one dihalogen compound selected from the group consisting of 4,4'-dichlorodiphenyl sulfone (DCPDS) and 4,4'-difluorodiphenyl sulfone (DFDPS), at least one carbonate component, in a solvent.

The monomer (a1) is preferably according to formula (IV):

(IV)

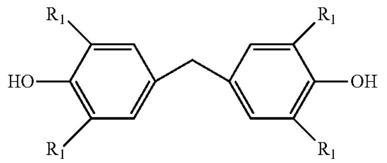

wherein each $R_1$, independently at each location, is an alkyl having from 1 to 5 carbon atoms, preferably methyl at each location.

In formula (I) to (IV) above, $R_1$ is preferably methyl at each location.

According to an embodiment, the PAES described in the present disclosure is obtained from the condensation of the aromatic dihydroxy monomer (a) which comprises at least 50 mol. % of monomer (a1), based on the total moles of aromatic dihydroxy monomer. For example at least 60 mol. %, at least 70 mol. %, at least 80 mol. %, at least 90 mol. %, at least 95 mol. % or at least 99 mol. % of the aromatic dihydroxy monomer (a) comprises monomer (a1). According to a preferred embodiment, the aromatic dihydroxy monomer (a) consists essentially of monomer (a1).

According to an embodiment, the PAES described in the present disclosure is obtained from the condensation of an aromatic dihalogen sulfone monomer (b), which comprises at least 50 mol. % of 4,4'-dichlorodiphenyl sulfone (DCPDS), based on the total moles of aromatic dihalogen sulfone monomer. For example at least 60 mol. %, at least 70 mol. %, at least 80 mol. %, at least 90 mol. %, at least 95 mol. %, at least 99 mol. % of the aromatic dihalogen sulfone monomer (b) comprises DCDPS.

According to a preferred embodiment, the aromatic dihalogen sulfone monomer (b) consists essentially of DCPDS.

The molar ratio of monomers (a) to (b) may vary between 0.9 and 0.1. For example the molar ratio of (a) to (b) may vary between 1.01 to 1.05.

The solvent used to prepare the PAES described herein may be selected from a group consisting of dimethylsulfoxide (DMSO), dimethylsulfone (DMS), diphenylsulfone (DPS), 1,3-dimethyl-2-imidazolidinone (DMI), diethylsulfoxide, diethylsulfone, diisopropylsulfone, tetrahydrothiophene-1, 1-dioxide, tetrahydrothiophene-1-monoxide, N-methylpyrrolidone (NMP), N-butylpyrrolidone (NBP), N-ethyl-2-pyrrolidone, N,N-dimethylformamide (DMF), N,N dimethylacetamide (DMAC), tetrahydrofuran (THF), toluene, benzene, chlorobenzene, dichlorobenzene, anisole, chloroform, dichloromethane (DCM), sulfolane, and mixtures thereof.

When the PAES polymer of the present invention comprises sulfonated recurring units, for example derived from sulfonated DCDPS (with the proviso that in this case the molar of recurring units deriving from sulfonated DCDPS is less than 40 mol. %), the solvent is preferably selected from a group consisting of dimethylsulfone (DMS), diphenylsulfone (DPS), 1,3-dimethyl-2-imidazolidinone (DMI), diethylsulfoxide, diethylsulfone, diisopropylsulfone, tetrahydrothiophene-1, 1-dioxide, tetrahydrothiophene-1-monoxide, N-methylpyrrolidone (NMP), N-butylpyrrolidone (NBP), N-ethyl-2-pyrrolidone, N,N-dimethylformamide (DMF), N,N dimethylacetamide (DMAC), tetrahydrofuran (THF), benzene, chlorobenzene, dichlorobenzene, anisole, chloroform, dichloromethane (DCM), sulfolane, and mixtures thereof, more preferably sulfolane or NMP.

The condensation process described herein may be carried out in the presence of a carbonate component which is selected in the group of alkali metal hydrogencarbonates, for example sodium hydrogencarbonate ($NaHCO_3$) and potassium hydrogencarbonate ($KHCO_3$), or in the group of alkali metal carbonate, for example potassium carbonate ($K_2CO_3$) and sodium carbonate ($Na_2CO_3$). Preferably the process of the present invention is carried out in the presence of potassium carbonate ($K_2CO_3$), sodium carbonate ($Na_2CO_3$) or a blend of both. According to an embodiment, the process of the present invention is carried out in the presence of a low particle size alkali metal carbonate, for example comprising anhydrous $K_2CO_3$, having a volume-averaged particle size of less than about 100 μm, for example less than 45 μm, less than 30 μm or less than 20 μm. According to a preferred embodiment, the process of the present invention is carried out in in the presence of a carbonate component comprising not less than 50 wt. % of $K_2CO_3$ having a volume-averaged particle size of less than about 100 μm, for example less than 45 μm, less than 30 μm or less than 20 μm, based on the overall weight of the base component in reaction mixture. The volume-averaged particle size of the carbonate used can for example be determined with a Mastersizer 2000 from Malvern on a suspension of the particles in chlorobenzene/sulfolane (60/40).

The molar ratio of carbonate component:dihydroxy monomer (a) may be from 1.0 to 1.2, for example from 1.01 to 1.15 or from 1.02 to 1.1. The molar ratio of carbonate component:dihydroxy monomer (a) is preferably of 1.05 or higher, for example 1.06 or 1.08.

According to the condensation reaction, the components of the reaction mixture are generally reacted concurrently. The reaction is preferably conducted in one stage. This means that the deprotonation of monomer (a) and the condensation reaction between the monomers (a) and (b) takes place in a single reaction stage without isolation of the intermediate products.

According to an embodiment of the process of the present invention, the condensation is carried out in a mixture of a polar aprotic solvent and a solvent which forms an azeotrope with water. The solvent which forms an azeotrope with water includes aromatic hydrocarbons such as benzene, toluene, xylene, ethylbenzene, chlorobenzene and the like. It is preferably toluene or chlorobenzene. The azeotrope forming solvent and polar aprotic solvent are used typically in a weight ratio of from about 1:10 to about 1:1, preferably from about 1:5 to about 1:1. Water is continuously removed from the reaction mass as an azeotrope with the azeotrope forming solvent so that substantially anhydrous conditions are maintained during the polymerization. The azeotrope-forming solvent, for example, chlorobenzene, is removed from the reaction mixture, typically by distillation, after the water formed in the reaction is removed leaving the PAES dissolved in the polar aprotic solvent.

Preferably, the reaction mixture ($R_G$) does not comprise any substance which forms an azeotrope with water.

In some embodiments, the process is such that the conversion (C) is at least 95%.

The temperature of the reaction mixture is kept at about 150° C. to about 350° C., preferably from about 210° C. to about 300° C. for about one to 15 hours.

The reaction mixture is polycondensed, within the temperature range, until the requisite degree of condensation is reached. The polycondensation time can be from 0.1 to 10 hours, preferably from 0.2 to 4 or from 0.5 to 2 hours, depending on the nature of the starting monomers and on the selected reaction conditions.

The inorganic constituents, for example sodium chloride or potassium chloride or excess of base, can be removed, before or after isolation of the PAES, by suitable methods such as dissolving and filtering, screening or extracting.

According to an embodiment, the amount of PAES at the end of the condensation is at least 30 wt. % based on the total weight of the PAES and the polar aprotic solvent, for example at least 35 wt. % or at least or at least 37 wt. % or at least 40 wt. %.

At the end of the reaction, the PAES polymer is separated from the other components (salts, base, . . . ) to obtain a PAES solution. Filtration can for example be used to separate the PAES polymer from the other components. The PAES solution can then be used as such for step (b) or alternatively, the PAES can be recovered from the solvent, for example by coagulation or devolatilization of the solvent.

The PAES polymer described herein may be characterized by its weight average molecular weight (Mw). The PAES described herein is advantageously characterized in that its weight average molecular weight (Mw) ranges between 70,000 g/mol and 200,000 g/mol, for example between 75,000 g/mol and 190,000 g/mol or between 80,000 g/mol and 180,000 g/mol.

The weight average molecular weight (Mw) of the PAES is determined by Size Exclusion Chromatography (SEC) using Methylene Chloride as a mobile phase.

The Membrane

The membrane of the present invention is used for purifying a biological fluid, preferably blood.

The membrane preferably contains less than 0.1 wt. % of 4,4'-dihydroxydiphenyl sulfone (BPS) and 4,4'-isopropylidenediphenol (BPA).

The term "membrane" is used herein in its usual meaning, that is to say it refers to a discrete, generally thin, interface that moderates the permeation of chemical species in contact with it. This interface may be molecularly homogeneous, that is, completely uniform in structure (dense membrane), or it may be chemically or physically heterogeneous, for example containing voids, holes or pores of finite dimensions (porous membrane).

According to the present invention, a membrane is typically a microporous membrane which can be characterized by its average pore diameter and porosity, i.e. the fraction of the total membrane that is porous.

The membrane of the present invention may have a gravimetric porosity (%) of 20 to 90% and comprises pores, wherein at least 90% by volume of the said pores has an average pore diameter of less than 5 μm. Gravimetric porosity of the membrane is defined as the volume of the pores divided by the total volume of the membrane.

Membranes having a uniform structure throughout their thickness are generally known as symmetrical membranes; membranes having pores which are not homogeneously distributed throughout their thickness are generally known as asymmetric membranes. Asymmetric membranes are characterized by a thin selective layer (0.1-1 μm thick) and a highly porous thick layer (100-200 μm thick) which acts as a support and has little effect on the separation characteristics of the membrane.

Membranes can be in the form of a flat sheet or in the form of tubes.

Tubular membranes are classified based on their dimensions in tubular membranes having a diameter greater than 3 mm; capillary membranes, having a diameter comprised between 0.5 mm and 3 mm; and hollow fibers having a diameter of less than 0.5 mm. Capillary membranes are otherwise referred to as hollow fibers.

Hollow fibers are particularly advantageous in applications where compact modules with high surface areas are required.

The membranes according to the present invention can be manufactured using any of the conventionally known membrane preparation methods, for example, by a solution casting or solution spinning method.

Preferably, the membranes according to the present invention are prepared by a phase inversion method occurring in the liquid phase, said method comprising the following steps:

(i) preparing a PAES polymer solution comprising the PAES described herein and a polar solvent,
(ii) processing said solution into a film;
(iii) contacting said film with a non-solvent bath.

The membrane of the present invention may comprise the PAES described herein in an amount of at least 1 wt. %, for example at least 5 wt. %, at least 10 wt. %, at least 15 wt. %, at least 20 wt. %, at least 25 wt. %, or at least 30 wt. %, based on the total weight of the polymer composition (C).

The membrane of the present invention may comprise the PAES described herein in an amount of more than 50 wt. %, for example more than 55 wt. %, more than 60 wt. %, more than 65 wt. %, more than 70 wt. %, more than 75 wt. %, more than 80 wt. %, more than 85 wt. %, more than 90 wt. %, more than 95 wt. % or more than 99 wt. %, based on the total weight of the polymer composition (C).

According to an embodiment, the membrane of the present invention may comprise the PAES described herein in an amount ranging from 1 to 99 wt. %, for example from 3 to 96 wt. %, from 6 to 92 wt. % or from 12 to 88 wt. %, based on the total weight of the polymer composition (C).

The membrane of the present invention may further comprise at least one polymer distinct form the PAES described herein, for example another sulfone polymer, e.g. polysulfone (PSU), polyethersulfone (PES), or a polyphenylene sulfide (PPS), a poly(aryl ether ketone) (PAEK), e.g. a poly(ether ether ketone) (PEEK), a poly(ether ketone ketone) (PEKK), a poly(ether ketone) (PEK) or a copolymer of PEEK and poly(diphenyl ether ketone) (PEEK-PEDEK copolymer), polyetherimide (PEI), and/or polycarbonate (PC). The other polymeric ingredient can also be polyvinylpyrrolidone and/or polyethylene glycol.

The membrane of the present invention may also further comprise at least one non polymeric ingredient such as a solvent, a filler, a lubricant, a mould release, an antistatic agent, a flame retardant, an anti-fogging agent, a matting agent, a pigment, a dye and an optical brightener.

Purification Method for a Biological Fluid

The purification method comprises at least a filtration step through the membrane described herein.

Preferably, the purification method is for purifying a human biological fluid, preferably a blood product, such as whole blood, plasma, fractionated blood components or mixtures thereof, that are carried out in an extracorporeal circuit. The extracorporeal circuit for carrying out a method comprises at least one filtering device (or filter) comprising at least one membrane as described above.

As intended herein, a blood purification method through an extracorporeal circuit comprises hemodyalisis (FD) by diffusion, hemofiltration (HF), hemodyafiiltration (HDF) and hemoconcentration. In HF, blood is filtered by ultrafiltration, while in HDF blood is filtered by a combination of FD and HF.

Blood purification methods through an extracorporeal circuit are typically carried out by means of a hemodyalizer, i.e. equipment designed to implement any one of FD, HF or HFD. In such methods, blood is filtered from waste solutes and fluids, like urea, potassium, creatinine and uric acid, thereby providing waste solutes- and fluids-free blood.

Typically, a hemodyalizer for carrying out a blood purification method comprises a cylindrical bundle of hollow fibers of membranes, said bundle having two ends, each of them being anchored into a so-called potting compound, which is usually a polymeric material acting as a glue which keeps the bundle ends together. Potting compounds are known in the art and include notably polyurethanes. By applying a pressure gradient, blood is pumped through the bundle of membranes via the blood ports and the filtration product (the “dialysate”) is pumped through the space surrounding the filers.

Polymer Solution for Preparing a Membrane

An aspect of the present invention is directed to a polymer solution for preparing a membrane comprises:

a) at least a poly(aryl ether sulfone) (PAES) polymer comprising recurring units ($R_{PAES}$) of formula (I):

(I)

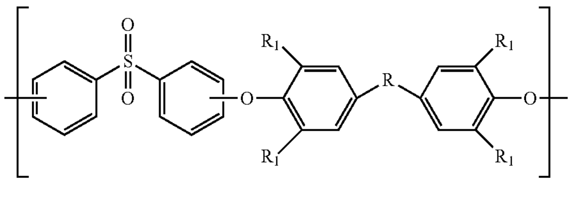

wherein:

each $R_1$ is, independently at each location, an alkyl having from 1 to 5 carbon atoms, and R is an alkylene having from 1 to 10 carbon atoms or a cycloalkylene having from 5 to 8 carbon atoms, and b) at least one polar solvent.

The overall concentration of the polymer (PAES) in the solution is preferably at least 8 wt. %, more preferably at least 12 wt. %, based on the total weight of the solution.

Typically, the concentration of the polymer (PAES) in the solution does not exceed 50 wt. %; preferably, it does not exceed 40 wt. %; more preferably, it does not exceed 30 wt. %, based on the total weight of the solution (SP).

The term "solvent" is used herein in its usual meaning, that is it indicates a substance capable of dissolving another substance (solute) to form an uniformly dispersed mixture at the molecular level. In the case of a polymeric solute it is common practice to refer to a solution of the polymer in a solvent when the resulting mixture is transparent and no phase separation is visible in the system. Phase separation is taken to be the point, often referred to as "cloud point", at which the solution becomes turbid or cloudy due to the formation of polymer aggregates.

Exemplary solvents are described in patent application WO 2019/048652 (Solvay Specialty Polymers USA).

The overall concentration of the solvent in the solution may be at least 20 wt. %, preferably at least 30 wt. %, based on the total weight of the solution. Typically the concentration of the solvent in the solution does not exceed 70 wt. %; preferably, it does not exceed 65 wt. %; more preferably, it does not exceed 60 wt. %, based on the total weight of the solution.

The solution may contain additional components, such as nucleating agents, fillers and the like.

The solution may also contain pore forming agents, notably polyvinylpyrrolidone (PVP), and polyethyleneglycol (PEG) having a molecular weight of at least 200.

Should the disclosure of any patents, patent applications, and publications which are incorporated herein by reference conflict with the description of the present application to the extent that it may render a term unclear, the present description shall take precedence.

Exemplary embodiments will now be described in the following non-limiting examples.

EXAMPLES

The disclosure will be now described in more detail with reference to the following examples, whose purpose is merely illustrative and not intended to limit the scope of the disclosure.

Starting Materials

- Tetramethylbisphenol F, commercially available from TCI America DCDPS (4,4'-dichlorodiphenyl sulfone), commercially available from Solvay Specialty Polymers USA, LLC
- $K_2CO_3$, commercially available from Aldrich
- Sulfolane, commercially available from Aldrich
- DMI (1,3-dimethyl-2-imidazolidinone), commercially available from TCI America
- Chlorobenzene, commercially available from Aldrich
- DMSO (dimethylsulfoxide), commercially available from Fisher
- Udel® P3500, commercially available from Solvay Specialty Polymers USA, LLC
- DSDCDPS (di-sulfonated 4,4'-dichlorodiphenyl sulfone), commercially available from Akron Polymer Systems Preparation of Polymers

Example 1

To a 1-L resin flask equipped with an overhead agitator, a nitrogen dip-tube, dean-stark trap with reflux condenser was charged 115.358 g (0.450 mol) of Tetramethylbisphenol F, 129.223 g (0.450 mol) of DCPDS, 65.302 g (0.473 mol) of $K_2CO_3$ and 494.11 g sulfolane. Agitation and nitrogen flow were established and the reaction mixture was purged with nitrogen for 15 minutes before starting heat via external oil bath with a target internal temperature of 200° C. Water, a byproduct of the polymerization reaction, was continuously stripped out of the reactor and collected in the dean-stark trap. Upon reaching 200° C., the reaction was held at that temperature until the desired Mw was achieved. Once desired molecular weight was achieved the polymerization was terminated by bubbling gaseous methylchloride through the reaction mixture at a rate of 1 g/min over 30-60 minutes. The reaction mixture was diluted with 317.64 g of sulfolane. The dilute polymer solution was filtered through a 2.7 μm glass fiber filter pad under pressure to remove salts. The polymer solution was precipitated in methanol or methanol/acetone (1:1) a ratio of 1:5 polymer solution to non-solvent to afford a white solid. The isolated white solid was then washed with the same non-solvent 6 times, vacuum filtered, and dried for 12 h in a vacuum oven at 100° C. The molecular weight was measured by GPC.

Example 2

The polymerization was carried out as per Example 1, however, the polymerization was terminated at a lower Mw.

Example 3

The polymerization was carried out as per Example 1, except the charge amounts were as follows:

Tetramethylbisphenol F—179.445 g (0.700 mol)
DCDPS—201.013 g (0.700 mol)
Potassium carbonate—101.581 (0.735 mol)
Sulfolane—494.107 g Once target Mw was reached, 768.61 g of sulfolane was added to dilute before filtration, coagulation, washing and drying.

Example 4

To a 1-L resin flask equipped with an overhead agitator, a nitrogen dip-tube, dean-stark trap with reflux condenser was charged 170.66 g (0.666 mol) of Tetramethylbisphenol F, 191.172 g (0.0.666 mol) of DCPDS, 96.607 g (0.699 mol) of K2CO3 and 313.28 g DMI. Agitation and nitrogen flow were established and the reaction mixture was purged with nitrogen for 15 minutes before starting heat via external oil bath with a target internal temperature of 195° C. Water, a byproduct of the polymerization reaction, was continuously stripped out of the reactor and collected in the dean-stark trap. Upon reaching 195° C., the reaction was held at that temperature until the desired Mw was achieved. Once desired molecular weight was achieved the polymerization was terminated by bubbling gaseous methylchloride through the reaction mixture at a rate of 1 g/min over 30-60 minutes. The reaction mixture was diluted with 714.86 g of DMI. The dilute polymer solution was filtered through a 2.7 μm glass fiber filter pad, under pressure, to remove salts. The polymer solution was precipitated in methanol or methanol/acetone (1:1) a ratio of 1:5 polymer solution to non-solvent to afford a white solid. The isolated white solid was then washed with the same non-solvent 6 times, vacuum filtered, and dried for 12 h in a vacuum oven at 100° C.

Example 5

To a 1-L resin flask equipped with an overhead agitator, a nitrogen dip-tube, dean-stark trap with reflux condenser was charged 179.445 g (0.700 mol) of Tetramethylbisphenol F, 201.013 g (0.700 mol) of DCPDS, 101.581 g (0.735 mol) of K2CO3 and 329.40 g NMP. Agitation and nitrogen flow were established and the reaction mixture was purged with nitrogen for 15 minutes before starting heat via external oil bath with a target internal temperature of 195° C. Water, a byproduct of the polymerization reaction, was continuously stripped out of the reactor and collected in the dean-stark trap. Upon reaching 195° C., the reaction was held at that temperature until the desired Mw was achieved. Once desired molecular weight was achieved the polymerization was terminated by bubbling gaseous methylchloride through the reaction mixture at a rate of 1 g/min over 30-60 minutes. The reaction mixture was diluted with 988.21 g of NMP. The dilute polymer solution was filtered through a 2.7 μm glass fiber filter pad, under pressure, to remove salts. The polymer solution was precipitated in methanol or methanol/acetone (1:1) a ratio of 1:5 polymer solution to non-solvent to afford a white solid. The isolated white solid was then washed with the same non-solvent 6 times, vacuum filtered, and dried for 12 h in a vacuum oven at 100° C.

Example 6

To a 1-L resin flask equipped with an overhead agitator, a nitrogen dip-tube, a barrett trap with reflux condenser was charged 153.81 g (0.600 mol) of tetramethylbisphenol F, 430.67 g of chlorobenzene, and 73.43 g of DMSO. Agitation and nitrogen flow were established and the reaction mixture was purged with nitrogen for 15 minutes before starting heat via external oil bath. When the temperature reached ~40° C., 94.84 g aqueous caustic solution (~50 wt %) followed by 260.34 g DMSO was added to the reactor. The internal temperature was slowly increased to ~150° C. while continuously removing water/chlorobenzene. Once all the water of the reaction was removed, a solution of 172.30 g of DCDPS in 172.30 g of chlorobenzene was added to the reactor slowly. After the addition was complete the reaction temperature was raised to 165-170° C. and held until high molecular weight was achieved. The polymerization was terminated with gaseous methyl chloride for 60 min, followed by dilution with chlorobenzene. The dilute polymer solution was filtered through a 2.7 μm glass fiber filter pad, under pressure, to remove salts. The polymer solution was precipitated in methanol or methanol/acetone (1:1) a ratio of 1:5 polymer solution to non-solvent to afford a white solid. The isolated white solid was then washed with the same non-solvent 6 times, vacuum filtered, and dried for 12 h in a vacuum oven at 100° C.

Example 7 in DMSO/Toluene

This example illustrates the preparation of the polymer according to example 8 of WO 2018/079733 (Mitsui).

To a 1-L resin flask equipped with an overhead agitator, a nitrogen dip-tube, dean-stark trap with reflux condenser was charged 57.68 g (0.225 mol) of Tetramethylbisphenol F, 38.77 g (0.135 mol) of DCPDS, 44.21 g (0.090 mol) of disulfonated DCDPS, 38.87 g (0.2813 mol) of $K_2CO_3$, 535.2 g DMSO, and 178.40 g of toluene. The nitrogen flow was established and the reactor contents were heated to 130° C. The azeotropic dehydration was carried out for 12 hours. Water was removed from the dean-stark trap and toluene was allowed to return to the reactor during this time. After 12 hours, toluene was distilled off and the temperature of the reaction mixture was allowed to reach 160° C. The polymerization was carried out at 160° C. for 12 hours. After 12 hours, the reactor was diluted with a total of 570 g toluene. A small portion of the reactor solution was filtered and used for GPC measurements.

Example 8 in NMP—10 Mol % Disulfonated DCDPS

To a 1-L resin flask equipped with an overhead agitator, a nitrogen dip-tube, dean-stark trap with reflux condenser was charged 128.14 g (0.500 mol) of Tetramethylbisphenol F, 129.22 g (0.450 mol) of DCPDS, 24.56 g (0.050 mol) of disulfonated DCDPS, 73.94 g (0.535 mol) of $K_2CO_3$, 300.05 g NMP. The reactor contents were purged with nitrogen for 15 minutes followed by heating to 190° C. After ~18 hours, the reaction was quenched with 150 g NMP and terminated with methyl chloride gas for 30 minutes. It was further diluted with 941 g of NMP. The polymer mixture was filtered and coagulated into a 5% NaCl water solution at a ratio of 1:10 (polymer solution:salt solution). It was washed 4-5 times with 5% sodium chloride salt water solution, filtered, and dried in a vacuum oven at 120° C. A small part of the filtered reaction solution was used for GPC measurement.

Example 9 in Sulfolane 10 Mol % Disulfonated DCDPS

To a 1-L resin flask equipped with an overhead agitator, a nitrogen dip-tube, dean-stark trap with reflux condenser was charged 128.14 g (0.500 mol) of Tetramethylbisphenol F, 129.22 g (0.450 mol) of DCPDS, 24.56 g (0.050 mol) of disulfonated DCDPS, 73.94 g (0.535 mol) of $K_2CO_3$, 368.24 g sulfolane. The reactor contents were purged with nitrogen for 15 minutes followed by heating to 225° C. After ~8 hours, the reaction was quenched with 150 g sulfolane and terminated with methyl chloride gas for 30 minutes. It was further diluted with 941 g of sulfolane and filtered while hot. The coagulated into a 5% NaCl water solution at a ratio of 1:10 (polymer solution:salt solution). It was washed 4-5 times with 5% sodium chloride salt water solution, filtered, and dried in a vacuum oven at 120° C. A small part of the filtered reaction solution was used for GPC measurement.

Example 10 in Sulfolane 20 Mol % Disulfonated DCDPS

The polymer was obtained according to the same synthesis process of example 9, except that the number of moles of DSDCPDS was 0.100 mole (20 mol. %). 0.400 mol of DCDPS, and 383.55 g of sulfolane. The reaction time was ~14 hours.

Example 11 in Sulfolane 30 Mol % Disulfonated DCDPS

The polymer was obtained according to the same synthesis process of example 9, except that the number of moles of DSDCPDS was 0.150 mol (30 mol. %), 0.350 mol DCDPS, and 398.85 g sulfolane. The reaction time was ~15 hours.

Example 12 in Sulfolane 40 Mol % Disulfonated DCDPS

The polymer was obtained according to the same synthesis process of example 9, except that the number of moles of DSDCPDS was 0.200 mol (40 mol. %), 0.300 mol of DCDPS, and 414.16 g of sulfolane The reaction time was 17 hours.

Characterization of the Polymers

Determination of Molecular Weight

Size Exclusion Chromatography (SEC) was performed using Methylene Chloride as a mobile phase. Two 5 µm mixed D Size Exclusion Chromatography (SEC) columns with guard column from Agilent Technologies was used for separation. An ultraviolet detector of 254 nm is used to obtain the chromatogram. A flow rate of 1.5 ml/min and injection volume of 20 µL of a 0.2% w/v solution in mobile phase was selected.

Calibration was performed using 10 narrow calibration standards of Polystyrene obtained from Agilent Technologies (Peak molecular weight range: 371000 to 580).

Calibration Curve:

1) Type: Relative, Narrow calibration standard calibration

2) Fit: 3rd order regression.

Integration and calculation: Empower Pro GPC software manufactured by Waters used to acquire data, calibration and molecular weight calculation. Peak integration start and end points are manually determined from significant difference on global baseline.

For the copolymers made using disulfonated DCDPS, two MiniMIX-D SEC columns along with a guard column from Agilent Technologies were used. The mobile phase was DMAc with 0.1M LiBr. A UV detector set at 270 nm was used to obtain the chromatogram. A flow rate of 0.3 mL/min and an injection volume of 5 µl at a 0.2% w/v concentration were used.

Calibration was performed using 10 narrow calibration standards of Polystyrene obtained from Agilent Technologies (Peak molecular weight range: 364,000 to 580).

Calibration Curve:

1) Type: Relative, Narrow calibration standard calibration

2) Fit: 3rd order regression.

Integration and calculation: Empower 3 GPC software manufactured by Waters used to acquire data, calibration and molecular weight calculation. Peak integration start and end points are manually determined from significant difference on global baseline.

Solution Viscosity

A 25 w/w % polymer solution was prepared in HPLC grade N'N-dimethylacetamide. The polymer solution viscosity was measured by ThermoHaake Viscotester VT550 equipped with a ThermoHaake sensor system with MV-DIN and the stator, and a temperature vessel controlled by ThermoHaake DC-30 circulating bath. Calibration of the equipment was performed using certified viscosity standards. The solution viscosity was measured at 40° C. and at a shear rate of 30 $s^{-1}$.

DSC

DSC was used to determine glass transition temperatures (Tg). DSC experiments were carried out using a TA Instrument Q100. DSC curves were recorded by heating, cooling, re-heating, and then re-cooling the sample between 25° C. and 320° C. at a heating and cooling rate of 20° C./min. All DSC measurements were taken under a nitrogen purge. The reported Tg and Tm values were provided using the second heat curve unless otherwise noted.

Results

The data table below summarizes the Mw obtained, solution viscosity, and glass transition temperatures.

TABLE 1

| | Mw (g/mol) | Solution viscosity (Pa · s) | Tg (° C.) |
|---|---|---|---|
| Example 1 | 78,087 | 2,439 | nd |
| Example 2 | 44,029 | 369 | 232 |
| Example 3 | 100,848 | 4,360 | 237 |
| Example 4 | 76,417 | nd | 230 |
| Example 5 | 122,561 | nd | 234 |
| Example 6 | 68,813 | nd | 229 |

TABLE 2

| | Mw (g/mol) |
|---|---|
| Example 7 | 8,955 |
| Example 8 | 117,279 |
| Example 9 | 176,937 |
| Example 10 | 142,864 |
| Example 11 | 151,586 |
| Example 12 | 188,643 |

Preparation of Membranes

Two flat sheet membranes were prepared using the following procedure.

Membrane #1: A 20 wt % NMP solution of polymer obtained from Example 2 (inventive example) was filtered through 2.7 µm syringe filter. A film was manually casted on a glass plate with a 6 mil draw bar. The cast films were submerged in a water bath at maintained at room temperature. The membrane formed was allowed to separate from the glass plate. The membrane was washed in fresh deionized water by submerging in another bath for 1 h. They were then stored in a sample jar containing clean DI water.

Membrane #2: A membrane using Udel® P3500 as the polymer (comparative example) was similarly prepared.

Figure 2:
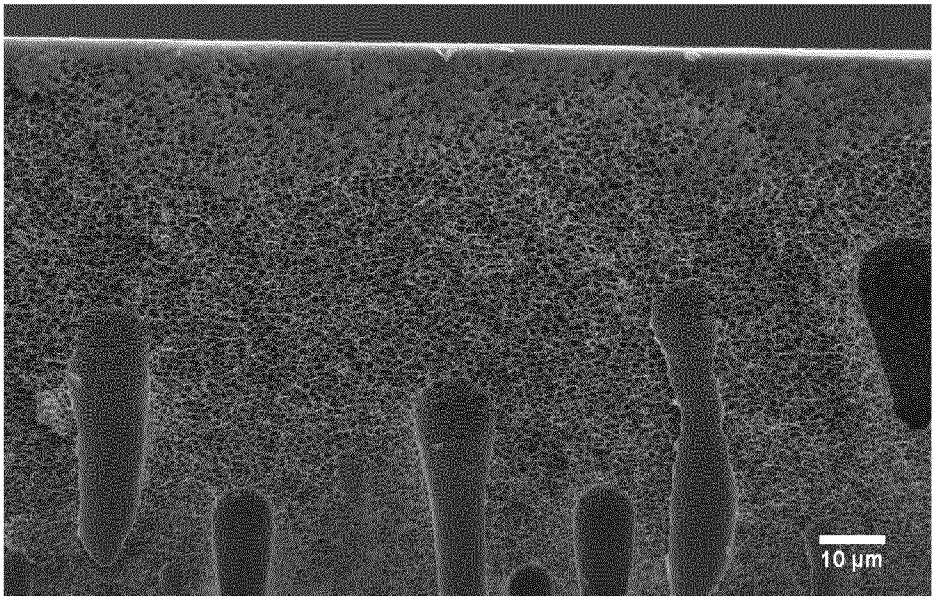
FIG. 2 is a picture of the membrane obtained with Udel® P3500, a polymer commercially available from Solvay Specialty Polymers USA. LLC (scale 50 μm)

Prior to being imaged by SEM, the membrane samples were pat dried then submerged in liquid nitrogen for 1 minute. Samples were then fractured. Fractured samples were added to an aluminum stub then sputter coated with AuPd. Transverse cross-section pictures of these membranes are shown on FIGS. 1 and 2.

The morphology of the membrane made from the inventive polymer is comparable in structure to the one made using Udel P3500.

Contact Angle

The contact angle of the films was measured using a KRÜSS EASYDROP instrument according to ASTM D5946-09.

TABLE 2

| | Contact angle |
|---|---|
| Membrane 1 | 85.7 ± 0.38 |
| Membrane 2 | 88.4 ± 0.79 |

The invention claimed is:

1. A membrane for purifying a biological fluid, comprising at least one poly(aryl ether sulfone) (PAES) polymer comprising recurring units ($R_{PAES}$) of formula (I):

(I)

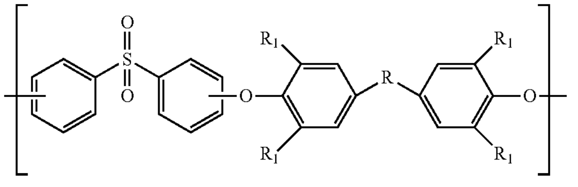

wherein:

each $R_1$ is, independently at each location, an alkyl having from 1 to 5 carbon atoms, and R is an alkylene having from 1 to 10 carbon atoms or a cycloalkylene having from 5 to 8 carbon atoms, wherein the weight average molecular weight (Mw) of the PAES ranges between 70,000 g/mol and 200,000 g/mol, as determined by Size Exclusion Chromatography (SEC) using methylene chloride as a mobile phase; and wherein said membrane is a microporous membrane having a gravimetric porosity (%) of 20 to 90% and comprising pores wherein at least 90% by volume of said pores has an average pore diameter of less than 5 microns.

2. The membrane of claim 1, wherein the PAES polymer comprises at least 60 mol. % of said recurring units ($R_{PAES}$) of formula (I), based on the total number of moles in the PAES polymer.

3. The membrane of claim 1, wherein the membrane contains less than 0.1 wt. % of 4,4'-dihydroxydiphenyl sulfone (BPS) and 4,4'-isopropylidenediphenol (BPA).

4. The membrane of claim 1, wherein the membrane is in the form of a flat sheet; a tubular membrane, said tubular membrane being optionally a tubular membrane having a diameter greater than 3 mm; a capillary membrane having a diameter between 0.5 mm and 3 mm; or a hollow fiber having a diameter of less than 0.5 mm.

5. The membrane of claim 1, wherein the PAES polymer is obtained by condensation in a reaction mixture ($R_G$) of:

at least one aromatic dihydroxy monomer (a), comprising at least a monomer (a1) of formula (IV):

(IV)

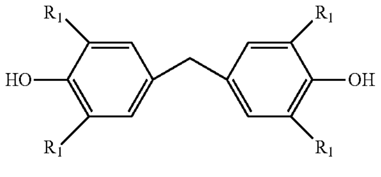

wherein $R_1$, independently at each location, is an alkyl having from 1 to 5 carbon atoms, at least one aromatic dihalogen sulfone monomer (b), comprising at least one dihalogen compound selected from the group consisting of 4,4'-dichlorodiphenyl sulfone (DCPDS) and 4,4'-difluorodiphenyl sulfone (DFDPS), and at least one carbonate component, in a solvent.

6. The membrane of claim 5, wherein the at least one aromatic dihydroxy monomer (a) comprises at least 50 mol. % of said monomer (a1), based on the total moles of said at least one aromatic dihydroxy monomer (a).

7. The membrane of claim 5, wherein said at least one aromatic dihalogen sulfone monomer (b) comprises at least 50 mol. % of 4,4'-dichlorodiphenyl sulfone (DCPDS), based on the total moles of said at least one aromatic dihalogen sulfone monomer (b).

8. The membrane of claim 5, wherein the solvent is selected from a group consisting of dimethylsulfoxide (DMSO), dimethylsulfone (DMS), diphenylsulfone (DPS), 1,3-dimethyl-2-imidazolidinone (DMI), diethylsulfoxide, diethylsulfone, diisopropylsulfone, tetrahydrothiophene-1,1-dioxide, tetrahydrothiophene-1-monoxide, N-methylpyrrolidone (NMP), N-butylpyrrolidone (NBP), N-ethyl-2-pyrrolidone, N,N-dimethylformamide (DMF), N,N dimethylacetamide (DMAC), tetrahydrofuran (THF), chlorobenzene, anisole, chloroform, dichloromethane (DCM), sulfolane, and mixtures thereof.

9. The membrane of claim 5, wherein the molar ratio of said at least one aromatic dihydroxy monomer to said at least one aromatic dihalogen sulfone monomer (b) is from 1.01 to 1.05.

10. The membrane of claim 1, wherein the PAES polymer comprises less than 1 mol. % of sulfonated recurring units, based on the total number of moles in the PAES polymer.

11. The membrane of claim 1, wherein the PAES polymer comprises at least 70 mol. % of recurring units ($R_{PAES}$) of formula (I), based on the total number of moles in the PAES polymer.

12. The membrane of claim 1, wherein the recurring units ($R_{PAES}$) are of formula (II):

(II)

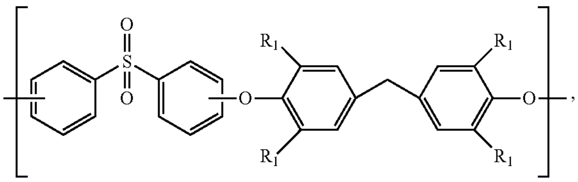, wherein $R_1$ is methyl at all locations.

13. A purification method for a biological fluid comprising at least a filtration step through the membrane of claim 1.

14. The method of claim 13, wherein the biological fluid is a blood product selected from the group consisting of whole blood, plasma, fractionated blood components or mixtures thereof.

15. The method of claim 13, which is carried out by means of an extracorporeal circuit.

16. The method of claim 15, wherein the extracorporeal circuit comprises a hemodialyzer, and the membrane is in the form of a cylindrical bundle of hollow fibers.

17. A microporous membrane for purifying a biological fluid, comprising at least one poly(aryl ether sulfone) (PAES) polymer comprising recurring unit ($R_{PAES}$) of formula (I):

(I)

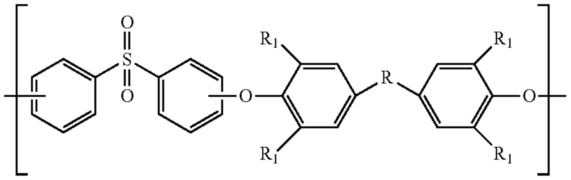

wherein:

each $R_1$ is a methyl group, and

R is an alkylene having from 1 to 10 carbon atoms or a cycloalkylene having from 5 to 8 carbon atoms, and further comprising sulfonated recurring unit ($R^*_{PAES}$) derived from sulfonated 4,4'-dichlorodiphenylsulfone and distinct from the recurring unit ($R_{PAES}$) of formula (II), in an amount of less than 40 mol. % based on the total number of moles in the PAES polymer, wherein the weight average molecular weight (Mw) of the PAES ranges between 70,000 g/mol and 200,000 g/mol, as determined by Size Exclusion Chromatography using methylene chloride as a mobile phase, and said microporous membrane having a gravimetric porosity (%) of 20 to 90% and comprises pores, wherein at least 90% by volume of said pores has an average pore diameter of less than 5 microns.

18. The microporous membrane of claim 17, wherein the recurring units ($R_{PAES}$) are of formula (II):

(II)

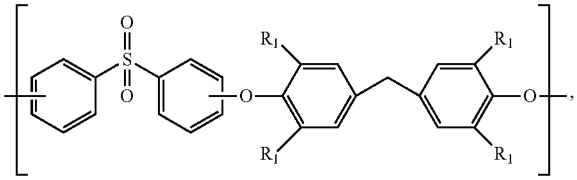, wherein $R_1$ is methyl at all locations.

* * * * *